United States Patent
Miner et al.

(10) Patent No.: US 8,282,608 B2
(45) Date of Patent: Oct. 9, 2012

(54) SELF PRIMING INTRAVENOUS DELIVERY SYSTEM

(75) Inventors: Tom M. Miner, Alpine, UT (US); Bryan G. Davis, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 905 days.

(21) Appl. No.: 11/852,080

(22) Filed: Sep. 7, 2007

(65) Prior Publication Data
US 2008/0097315 A1 Apr. 24, 2008

Related U.S. Application Data

(63) Continuation-in-part of application No. 11/205,236, filed on Aug. 16, 2005, now Pat. No. 7,722,577, and a continuation-in-part of application No. 10/768,760, filed on Jan. 29, 2004.

(60) Provisional application No. 60/654,705, filed on Feb. 18, 2005.

(51) Int. Cl.
*A61M 5/14* (2006.01)

(52) U.S. Cl. ...................................................... 604/251

(58) Field of Classification Search .................. 604/122, 604/251–255
See application file for complete search history.

(56) References Cited

U.S. PATENT DOCUMENTS

| | | | |
|---|---|---|---|
| 3,390,677 A | 7/1968 | Razimbaud | |
| 3,631,654 A | 1/1972 | Riely et al. | |
| 4,013,072 A * | 3/1977 | Jess | 604/252 |
| 4,198,971 A | 4/1980 | Noiles | |
| 4,200,095 A | 4/1980 | Reti | |
| 4,227,527 A | 10/1980 | De Frank et al. | |
| 4,396,016 A * | 8/1983 | Becker | 604/126 |
| 4,571,244 A * | 2/1986 | Knighton | 604/118 |

(Continued)

FOREIGN PATENT DOCUMENTS
WO WO 2004/020037 A1 3/2004

OTHER PUBLICATIONS

Braun, Product detail, http://www.bbraunoem-industrial.com/products/details.cfm?prodid=B0843225&id=Caps&area=C, p. 1, Apr. 12, 2005.

*Primary Examiner* — Kevin C Sirmons
*Assistant Examiner* — Bradley Osinski
(74) *Attorney, Agent, or Firm* — Mony R. Ghose; Craig Metcalf; Kirton McConkie

(57) ABSTRACT

A bubble free, self-priming IV set for use in the administration of liquids includes a coupling assembly for attaching the delivery system to a source of liquid and includes a coupling membrane for controlling the flow of liquid and air through the coupling assembly. The system also includes a drip chamber for receiving liquid through the coupling assembly, the drip chamber having a membrane for preventing air from leaving the drip chamber. A self leveling port is disposed within a wall of the drip chamber, the port being permeable to air, but impermeable to liquid. Finally, a patient conduit is in fluid communication with the drip chamber and further comprises a flow control plug disposed at the distal end of the conduit. The flow control plug is permeable to air but impermeable to liquid. Use of this system allows a clinician to attach a source of fluid to a patient without significant intervention, while the system self primes.

21 Claims, 3 Drawing Sheets

U.S. PATENT DOCUMENTS

| | | |
|---|---|---|
| 4,615,694 A | 10/1986 | Raines |
| 4,906,260 A | 3/1990 | Emheiser et al. |
| 5,242,424 A | 9/1993 | Chen |
| 5,290,253 A | 3/1994 | Kira |
| 5,308,314 A | 5/1994 | Fukui et al. |
| 5,489,385 A | 2/1996 | Raabe et al. |
| 5,603,706 A | 2/1997 | Wyatt et al. |
| 5,779,674 A | 7/1998 | Ford |
| 5,855,230 A | 1/1999 | Guala et al. |
| 5,954,957 A | 9/1999 | Chin-Loy et al. |
| 6,013,061 A | 1/2000 | Kelley |
| 6,336,916 B1 * | 1/2002 | Bormann et al. ............ 604/251 |
| 6,468,251 B1 | 10/2002 | Yamanaka et al. |
| 6,699,215 B2 | 3/2004 | Fujii |
| 6,972,000 B2 | 12/2005 | Kappel et al. |
| 2002/0156431 A1 * | 10/2002 | Feith et al. .................... 604/247 |
| 2005/0171491 A1 | 8/2005 | Minh Miner et al. |
| 2006/0189937 A1 | 8/2006 | Miner |

\* cited by examiner

SELF PRIMING INTRAVENOUS DELIVERY SYSTEM

CROSS-REFERENCED RELATED APPLICATIONS

This application is a continuation-in-part application of application Ser. No. 11/205,236, now U.S. Pat. No. 7,722,577 filed Aug. 16, 2005 and entitled "Bubble Free-Self Primed IV Set," which in turn claims the benefit of U.S. Provisional Application No. 60/654,705, filed Feb. 18, 2005. This application is also a continuation-in-part application of co-pending application Ser. No. 10/768,760 filed Jan. 29, 2004 and entitled "Intravenous Delivery System." Each of the above-referenced applications is incorporated herein by this reference.

BACKGROUND OF THE INVENTION

This invention relates generally to tubing sets used in the administration of liquids to a patient that are commonly referred to as intravascular ("IV") sets and more particularly concerns air bubble free (hereinafter referred to as simply "bubble free"), self-priming IV sets. An IV set is used broadly herein to describe, among other sets, tubing sets used in the arterial, intravenous, intravascular, peritoneal, and non-vascular administration of fluid. Of course, one of skill in the art may use IV set to administer fluids to other locations within a patient's body than those listed.

One common method of administering fluids into a patient's blood flow is through an IV set. An IV set is an apparatus that generally includes a connector for connection to a fluid reservoir, a drip chamber used to determine the flow rate of fluid from the fluid reservoir, tubing for providing a connection between the fluid reservoir and the patient, and a connector for attachment to a catheter that may be positioned intravenously in a patient. An IV set may also include a Y-connector or other access point or device that allows for the piggybacking of IV sets and for the administration of medicine from a syringe into the tubing of the IV set.

It is good practice to remove air from IV sets which access a patient's blood flow. While this concern is critical when accessing arterial blood, it is also a concern when accessing the venous side. Specifically, if air bubbles are allowed to enter a patient's blood stream while receiving the intravenous administration of liquids, the air bubbles can form an air embolism and cause serious injury to a patient.

In a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent as arterial blood flow throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an IV set for use in the intravenous administration of liquids, the complete removal of air bubbles can be a time consuming process. The process may also lead to contamination of the IV set by inadvertently touching a sterile end of the IV set. Typically, when an IV set is primed, a clamp is closed to prevent liquid from moving from a drip chamber through the tubing. The IV set is then attached to an IV bag or bottle. Once attached, the drip chamber, which is typically made of a clear flexible plastic, may be squeezed to draw the liquid out of the IV bag or bottle and into the drip chamber. The drip chamber is allowed to fill about ⅓ to ½ full when the clamp is opened to allow liquid to flow through the tube to an end of the IV set.

This initial process, however, typically traps air in tubing which must be removed. For example, the flow of the liquid through the tubing of the IV set may be turbulent and can entrap air within the tube as the boundary layer between the liquid and the tubing is sheared. The flow rate out of the drip chamber may be higher than the flow rate of liquid entering the drip chamber. This can cause a bubble ladder to form as air is sucked from the drip chamber into the tubing.

Additionally, air bubbles may be generated as drops of liquid strike the surface of the pool of liquid within the drip chamber. These air bubbles can be pulled into the tubing of the IV set from the drip chamber. This problem may be aggravated in pediatric applications where the drip orifice may be smaller which may result in increased turbulence.

To remove air bubbles from the IV set, liquid from the IV bag or bottle is allowed to flow through the tubing while an attendant taps the tubing to encourage the air bubbles out the end of the IV set. As the liquid is allowed to flow out of the IV set to clear air bubbles from the tubing, the liquid is generally allowed to flow into a waste basket or other receptacle. During this procedure the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the IV set. More specifically, if the IV set includes a Y-connector, air bubbles may be removed at the Y-connector by a syringe.

In some cases, a small pore filter may be used in the drip chamber to prevent air from entering the IV tubing from the drip chamber. However, the bubbles formed from the dripping action may become trapped on the filter, thus, reducing the flow of liquid through the filter to the IV tubing. However, the filter is normally positioned so that air may be trapped between the bottom of the filter and the bottom of the drip chamber.

Accordingly, a need exists for an IV set that is self-priming and bubble free, and which does not require constant attention and supervision. Additionally, a need exists for an IV set that prevents bubbles from entering the tubing during use, while providing flow rates that satisfy the needs of the patient.

BRIEF SUMMARY OF THE INVENTION

The apparatus of the present invention has been developed in response to the present state of the art, and in particular, in response to the problems and needs in the art that have not been fully solved by currently available IV sets. Thus, the present invention provides an IV set for use in intravenous administration of liquids that prevents air from being passed to a patient during the intravenous administration of liquids.

In accordance with the invention as embodied and broadly described herein in the preferred embodiment, an IV set is provided. According to one embodiment, the IV set may include a drip chamber having a chamber inlet and a chamber outlet and a bubble isolation membrane or other device disposed within the drip chamber that prevents air bubbles from exiting the chamber outlet. Typically, IV sets are gravity fed so that the chamber inlet is disposed in a top surface and the chamber outlet is disposed in a bottom surface of the drip chamber.

The side wall of the drip chamber may include an opening located at a height above the bottom wall, and a vent plug is provided for covering the opening. The vent plug allows air contained in the drip chamber which becomes displaced upon filling of the drip chamber to escape from the drip chamber through the vent plug.

Additionally, the IV set may include a means for venting air out of the patient conduit tube, such a flow control plug that has an air vent coupled to the outlet end of the patient conduit. The flow control plug may include a hydrophobic material, which allows air to exit the IV set while preventing liquid from exiting. The air vent may also include several small holes which allow air to pass while limiting the passage of liquid through the end plug. The end plug and the air vent acts as a flow restrictor to the exiting air, so that when a liquid is moving through the tube, the velocity of the liquid flow is controlled such that the flow is generally laminar. The laminar flow of the liquid through the tube prevents air from becoming entrapped within the tube during priming and helps to completely eliminate the air from the tube during priming.

The bubble isolation device or membrane includes means for preventing bubbles from exiting the chamber outlet and may include an active portion that comprises a hydrophilic filter or an absorbent structure, such as a sponge. The bubble isolation device may also include an absorbent structure that includes a woven material and/or a mat of material. The mat may be sintered or adhered together by an adhesive. Additionally, the bubble isolation device may include a concave surface that is disposed within the drip chamber so that the liquid entering the drip chamber through the chamber inlet is directed toward the concave surface.

Where the active portion of the bubble isolation device or membrane includes a hydrophilic filter or an absorbent structure, the bubble isolation device may be shaped to match the profile and abuts the bottom surface of the drip chamber so that the active portion completely covers the chamber outlet. By disposing the bubble isolation device against the bottom surface of the drip chamber, air is prevented from being trapped between the bubble isolation device and the bottom surface of the drip chamber.

Where the bubble isolation device includes a concave surface, the bubble isolation device may be disposed to partition the chamber into a bubble isolation chamber and a calm fluid chamber. The bubble isolation chamber is above the concave surface and the calm fluid chamber is positioned below the concave surface but above the bottom surface of the drip chamber. The concave surface directs bubbles toward the surface of the liquid to be expelled as new bubbles are formed by the droplets of liquid striking the surface of the liquid.

The IV set may also include a particulate filter to prevent solid material from exiting the tube. Additionally, the IV set may include a zero dead space access port disposed between the inlet end and the outlet end of the tube. A zero dead space access port is designed to substantially prevent the entrapment of air within the access port as liquid flows through the access port.

The system may include a further membrane within or above the drip chamber that provides an anti-run dry feature. In the vent fluid ceases to flow within the drip chamber the membrane maintains a safe level of residual fluid within the drip chamber.

A method for priming the IV set described above may include the steps of coupling the chamber inlet to a source of the liquid, wetting the bubble isolation device with liquid, and using the bubble isolation device to prevent air bubbles from reaching the chamber outlet. Additionally, the method may include the steps of opening the clamp to permit liquid to flow through the tube, using the end plug to restrict the venting of air from the tube as liquid flows through the tube so that the fluid flow through the tube is laminar, and using the end plug to prevent liquid from exiting the outlet end of the tube.

The method may include the steps of providing a self priming intravenous delivery system. The intravenous delivery system comprises a coupling assembly for attaching the delivery system to a source of liquid and including a coupling membrane for controlling the flow of liquid and air through the coupling assembly. The system also includes a drip chamber for receiving liquid through the coupling and having a membrane disposed therein for preventing air from leaving the drip chamber. As discussed above, the drip chamber may include a self leveling port disposed within a wall of the drip chamber being permeable to air until liquid contact, but impermeable to liquid. The system also includes a patient conduit in fluid communication with the drip chamber and comprising a flow control plug disposed at the distal end of the conduit, wherein the flow control plug is permeable to air but impermeable to liquid. A source of fluid is attached to the coupling assembly such that fluid flows into and through the delivery system but such that air is prevented from exiting the system once the system is primed. The priming of the device takes place without user intervention. The method may also include providing an adjustable clamp on the patient conduit and further comprising the step of closing the clamp.

As the configuration of the IV set varies, the method may also include additional steps. For example, where the bubble isolation device is an absorbent structure, the method may further include absorbing the liquid in the absorbent structure so that liquid does not pass the chamber outlet until the absorbent structure is saturated. Where the IV set includes a particulate filter, the method may include using the particulate filter to prevent material from the bubble isolation device from exiting the tube. Alternatively, where the tube includes a zero dead space access port, the method may include expelling all air from the zero dead space access port with the front of the liquid flowing through the tube.

Where the configuration of the IV set includes an end plug, the method may include the step of using the end plug to restrict the venting of air from the tube as liquid flows through the tube so that the volume of fluid flowing through the chamber inlet is greater than or about equal to the liquid flow through the chamber outlet until the self leveling port is closed. Alternatively, where the bubble isolation device includes a concave surface, the method may further include the steps of using the bubble isolation device to partition the chamber into a bubble isolation chamber and a calm fluid chamber and using the concave surface to retain the air bubbles in the bubble isolation chamber.

These and other features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scopes the invention will be described and explained with additional specificity and detail through the use of the accompanying drawings in which.

DETAILED DESCRIPTION OF THE INVENTION

Figure 2:
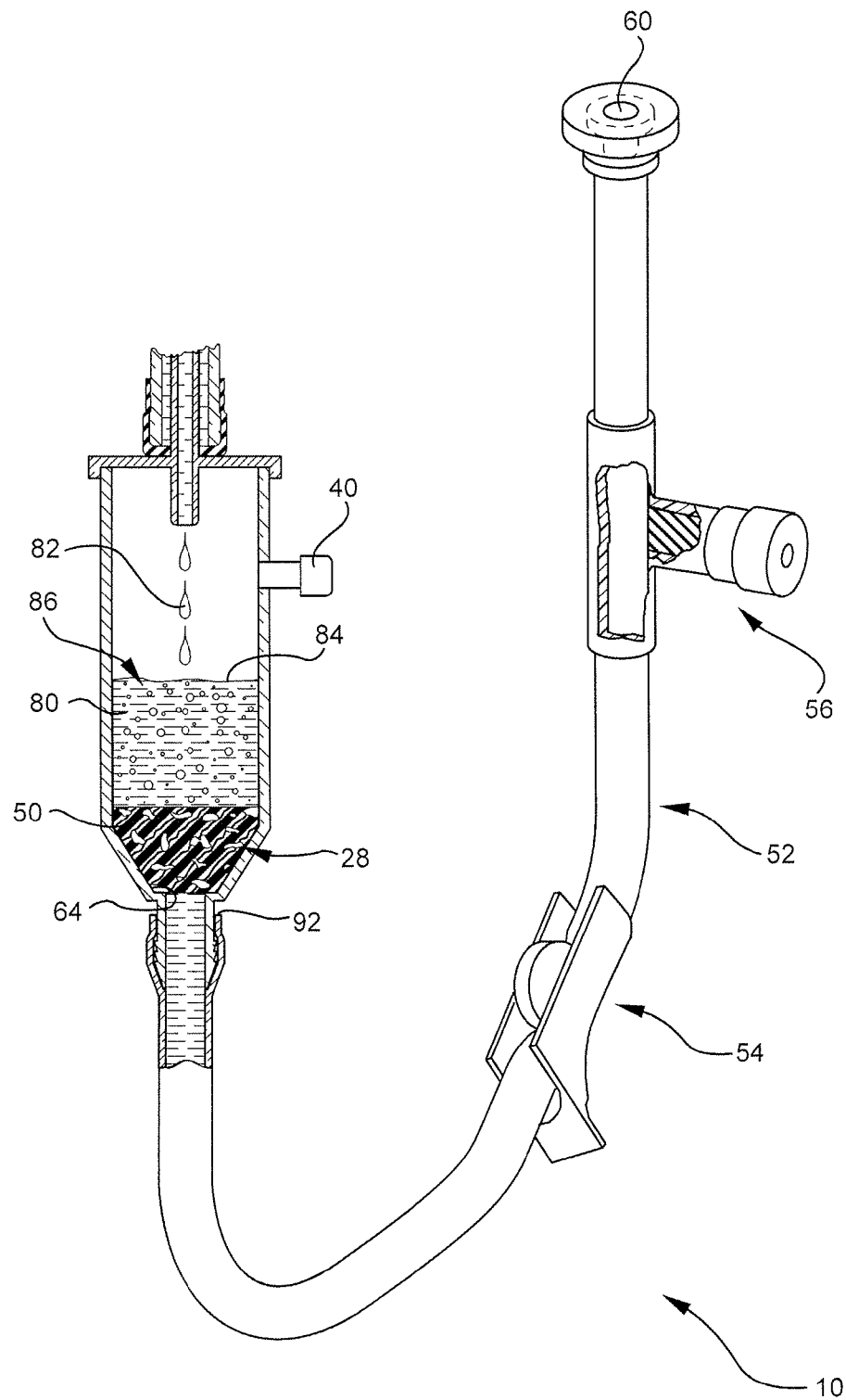
FIG. 2 is cross sectional view of the IV set of FIG. 1.
Figure 3:
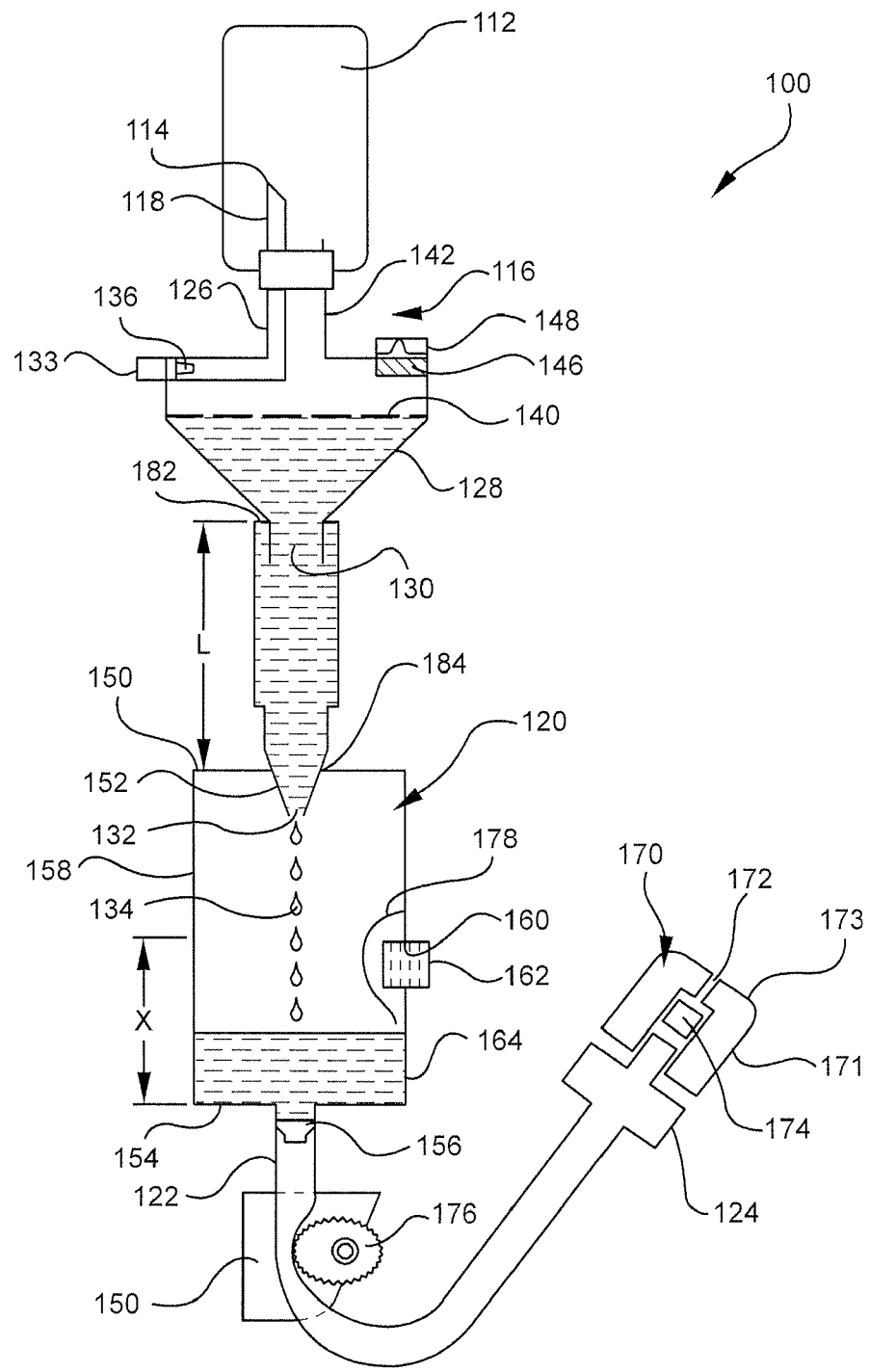
FIG. 3 is a cross sectional view of an alternative embodiment of an IV set.

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the self-priming intravenous delivery system of the present invention, as represented in FIGS. 1 through 3, is not intended to limit the scope of the invention, as claimed, but is merely representative of presently preferred embodiments of the invention.

For this application, the phrases "connected to," "coupled to," and "in communication with" refer to any form of interaction between two or more entities, including mechanical, electrical, magnetic, electromagnetic, and thermal interaction. The phrase "attached to" refers to a form of mechanical coupling that restricts relative translation or rotation between the attached objects.

The phrase "attached directly to" refers to a form of attachment by which the attached items are either in direct contact, or are only separated by a single fastener, adhesive, or other attachment mechanism. The term "abutting" refers to items that are in direct physical contact with each other, although the items may not be attached together. The terms "integrally formed" refer to a body that is manufactured integrally, i.e., as a single piece, without requiring the assembly of multiple pieces. Multiple parts may be integrally formed with each other if they are formed from a single work piece.

Figure 1:
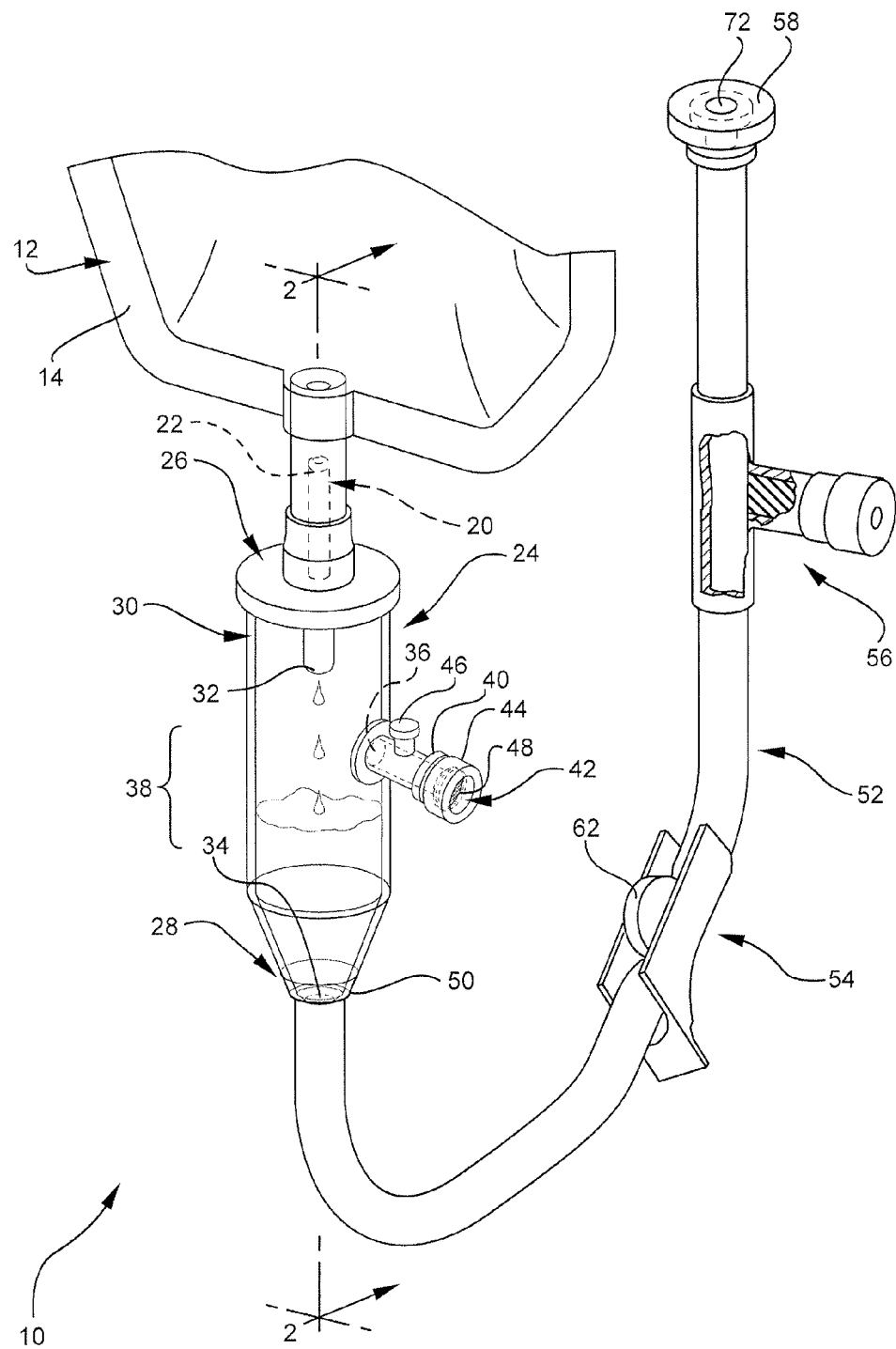
FIG. 1 is a perspective view of an IV set coupled to an IV bag.

Referring to FIG. 1, a perspective view illustrates an intravenous (IV) delivery system 10 according to the invention. As shown, the IV system 10 may be connected to a source of liquid 12, which in this configuration is an IV bag 14. Alternatively, the source of liquid 12 may be an IV bottle (not shown) or other container known in the art.

The IV system 10 may be connected to the IV bag 12 by a coupling 20 for connecting the IV system 10 to the IV bag 14. As shown, the coupling 20 may be a spike 22 for spiking the IV bag 14 and/or a threaded coupling (not shown).

The IV system 10 may include a drip chamber 24 for determining the flow rate from the source of liquid 12. The drip chamber 24 may include a top end 26, a bottom end 28, and a sidewall 30 extending between the top end 26 and the bottom end 28. The top end 26 may include an inlet orifice 32 that may be shaped and sized to encourage liquid entering the drip chamber 24 to form droplets, facilitating the determination of the liquid's flow rate. The bottom end 28 may also include an outlet orifice 34 that permits liquid to exit the drip chamber 24.

The drip chamber 24 may also include an access orifice 36. The access orifice 36 may be positioned in the top end 26 or in the sidewall 30. In some configurations, the access orifice 36 may be positioned at or near an operable liquid height 38 of the drip chamber 24. The operable liquid height 38 of the drip chamber 24 is deep enough so that air will not be sucked from the surface of the liquid into the outlet orifice 34, yet shallow enough that each droplet that falls from the inlet orifice 32 may be discerned in order to determine the flow rate of liquid into the drip chamber 24. For example, the operable liquid height 38 may range from about ⅓ to about ⅔ full. However, the preferable operable liquid height 38 of drip chamber 24 may range from about ⅓ to about ½ full.

A self leveling port 40 may be connected to the access orifice 36. The access port 40 may be used to removably connect the access orifice 36 to various devices 42, such as a cap 44, another IV set, a syringe, and other devices known in the art. As shown, the access port 40 may be a Luer fitting, known in the art.

A valve 46 may also be connected to the drip chamber 24 to selectively control access to the drip chamber 24 through the access orifice 36. The valve 46 may be a stop cock, a slide valve, a butterfly valve, or any other type of valve known in the art. The valve 46 may be opened to allow gravity to pull liquid from the source of liquid 12 into the drip chamber 24 without deforming the sidewall 30 of the drip chamber 24 to induce a vacuum. The valve 46 may remain open until the operable liquid height 38 is reached. When the valve 46 is closed, fluid may only enter and exit through the inlet orifice 32 and outlet orifice 34. Thus, when the valve 46 and the outlet orifice 34 are closed, the pressure within the drip chamber 24 may rise until the liquid is unable to enter the drip chamber 24 from the inlet orifice 32.

In configurations of the IV system 10 where the self leveling port 40 and the valve 46 are connected to the access orifice 36, the valve 46 may be disposed to prevent fluid from the self leveling port 40 from reaching the access orifice 36. For example, the valve 46 may be used to control the flow from another IV system connected to the self leveling port 40 into the drip chamber 24.

Additionally, a filter 48 may be connected to the access orifice 36, permitting air to flow through the filter 48 while restricting the flow of liquid. Where the access orifice 36 is disposed at an operable liquid height 38, the filter 48 may be used as a fail safe to prevent the height of liquid within the drip chamber 24 from exceeding the operable liquid height 38 of the drip chamber 24. More specifically, once the filter 48 is covered by the liquid within the drip chamber 24, the liquid and air in the drip chamber 24 is prevented from exiting the access orifice 36. Thus, the pressure may rise within the drip chamber 24 and prevent liquid from entering the drip chamber 24 from the source of liquid 12. In this configuration the filter 48 results in the self leveling port 40 being permeable to air, but impermeable to liquid, and becomes impermeable to air upon contact with liquid.

The IV system 10 may also include a membrane 50 disposed in the drip chamber 24. The membrane 50 is configured such that air is prevented from leaving the drip chamber 24. Thus, the membrane 50 acts as a bubble trap to trap any air bubbles that may otherwise flow out of the drip chamber 24 into the patient conduit 52.

A clamp 54, a zero dead space access port 56, and a flow control plug 58 may be attached to the tube 24. The clamp 54 permits the flow of liquid 14 exiting the drip chamber 20 to be controlled and stopped. The zero dead space access port 56 permits another IV set (not shown) to be piggybacked onto the IV set 10 or to have medication directly added to the fluid 14 by a syringe (not shown). The zero dead space access port 56 is also designed not to trap air as the liquid 14 flows through it. The flow control plug 58 helps to protect an end 72 of the IV system from contamination and also helps to prevent air bubbles from moving through the tube 24 with the liquid 14. In particular, the flow control plug 58 controls fluid flow in the patient conduit 52 during priming to reduce air bubble formation. The flow control plug 58 can include a housing that houses a single flow control material.

A clamp 54, a zero dead space access port 56, and a flow control plug 58 may be attached to the tube 24. The clamp 54 permits the flow of liquid 14 exiting the drip chamber 20 to be controlled and stopped. The zero dead space access port 56 permits another IV set (not shown) to be piggybacked onto the IV set 10 or to have medication directly added to the fluid 14 by a syringe (not shown). The zero dead space access port 56 is also designed not to trap air as the liquid 14 flows through it. The flow control plug 58 helps to protect an end 60 of the IV system from contamination and also helps to prevent air bubbles from moving through the tube 24 with the liquid 14. In particular, the flow control plug 58 controls fluid flow in the patient conduit 52 during priming to reduce air bubble formation.

Before the IV system 10 is attached to a source of liquid 14, the clamp 54 is typically opened, unlike conventional systems where the clamp is closed to prevent the flow of fluid through the patient conduit 52. As shown, the clamp 54 is a roller clamp 62. Other types of clamps may be used. The clamp may be pre-programmed to allowed fluid flow at a specific rate. Once the IV system 10 is attached to a source of liquid 14, it is unnecessary to produce a vacuum by squeezing the drip chamber 24 as is conventional.

Referring to FIG. 2, a cross sectional view illustrates the IV system and specifically the drip chamber 24 of FIG. 1. As shown, the membrane 50 conforms to the shape of the bottom end 28 of the drip chamber 20 and completely covers the chamber outlet 64. By positioning the membrane 50 to completely cover the chamber outlet 64, air is prevented from being trapped between the membrane 50 and the bottom end 28 as the fluid 14 moves through the membrane 50.

While in use, air bubbles 80 are generated as the droplets 82 strike the surface 84 of the pool 86. The membrane 50 prevents the air bubbles 80 from reaching the chamber outlet 64 so that the air bubbles 80 are able to return to the surface 84 of the pool 86 and be discharged or vented through the self leveling port 40. Also, the membrane may be made of molded open-cell foam that has a general pore size of about 10 to 20 microns with the preferred pore size being about 12 to 15 microns.

Also shown, the connection 90 between the patient conduit 52 and the drip chamber 24 is a zero dead space connection. In other words, the inlet end 92 is shaped to be attached flush to the chamber bottom end 28 so that air may not be entrapped at the connection 90 as the fluid 14 passes the connection 90 and purges the air from the patient conduit 52.

FIG. 3 depicts an alternative embodiment of a self priming IV delivery system 100 used for administering an IV-solution to a patient. As illustrated above, a source of liquid 112 is provided. The liquid is located in a container 114 such as a vented rigid container or bottle, or a collapsible plastic bag, as is discussed above . . . . The IV system 100 is a hermetically sealed system and includes a solution coupling spike assembly 116 having a lancing or piercing member 118 for piercing a seal on the container 114. As set forth above, other primary components of the IV system 10 include a drip chamber 120, and a patient conduit 122 having a termination end 124 and supporting a flow controller such as a roller clamp 126 for controlling the flow of liquid in the patient conduit 122.

The venting conduit 126 provides a sealable opening at an outer end for communicating with the surrounding atmosphere, i.e. with the environment in which the IV system 100 is disposed. When the spike assembly 116 is connected to a rigid container 112, such as a glass bottle, venting of the container is provided through the conduit 30 to allow the liquid to flow. If, on the other hand, the container 112 is a collapsible bag, venting is not required and the conduit 126 can remain sealed. As the liquid is drawn out by the piercing member 118 of the spike assembly 116, the liquid flows down into a funnel-shaped portion 128 having an outlet end 130 which supports a drip orifice 132 or which otherwise directs the liquid to the drip orifice for providing the liquid, in the form of a succession of individual drops, to the drip chamber 120.

The spike assembly 116 also includes a check valve 136 disposed at an outlet end of the venting conduit 126 and an air filter 138 disposed between the check valve 136 and the surrounding atmosphere, as shown. When the venting conduit is opened, as in the case of the piercing member 118 being coupled to a rigid container 114, the check valve allows filtered air, through air filter 138, to enter the venting conduit to cause liquid to flow out of the container, but prevents air, and consequently, liquid, from exiting the container 112 through the venting conduit 126. A membrane 140, which may be configured as a fine mesh screen, is also preferably included in the spike assembly 116. The membrane may be formed of any suitable material—such as polyamide nylon 6,6, polyamide nylon 11, or polyester-polyethylene teraphthalate with a hydrophilic coating applied by a plasma coating process—and causes a sealing off of the funnel portion 128 of the spike assembly from the fluid conduit 142 when the contents of the container 114 have been drained into the spike assembly 116. The sealing off is caused by the surface tension of the medicament forming a barrier on the membrane 140 which will prevent air present in the container 112 from being passed through to the drip chamber 120 and to the patient conduit 122. Thus, upon emptying of the container 114, the air present in the container will be confined to an area 144 above the membrane 140.

When a subsequent dose of medicament is required, the spike 118 of the spike assembly 116 is removed from the empty container 112 and attached to a full container. In order to start the flow of liquid from the subsequent container, the air confined in area 144 must be removed, and a venting membrane 146 is included in the spike assembly for this purpose. As liquid again flows from the second container 112, air will be forced out through the membrane 146. Membrane 146 may be comprised of a porous hydrophobic material such as polyethylene (PE), polypropylene (PP), or polytetrafluoroethylene (PTFE), so that air is allowed to pass from area 144 to the surrounding atmosphere while preventing liquid in the funnel portion 128 from spilling through the membrane, such as in the event of an overflow condition. Once the air is removed, the roller clamp 150 is opened to allow the fluid to flow into the patient line 122. A check valve 148 prevents air from the surrounding atmosphere from entering area 144 through membrane 144 when fluid flows from the container 112.

The drip chamber 120 includes a top wall providing an inlet opening, a bottom wall 154 providing an outlet opening 156, and at least one side wall 158 comprised of a transparent or translucent material so that medicament in the drip chamber can be readily viewed. A drip orifice or opening 132 may be formed on, attached to, or may depend from the top wall 150 or, alternatively, may be formed on the outlet end 130 of the spike assembly 116. As explained above, the drip orifice 132 establishes the size of the liquid drops 134 as the liquid enters the drip chamber 120. By adjusting the rate of flow of the drops 134 into the drip chamber 120, and knowing the size of the individual drops which is dictated by the drip orifice size, a medicament dosage rate can be established. The drip chamber 120 also includes an opening or hole 160 formed in the side wall 158 and vertically displaced from the drip chamber bottom 154 by a predetermined amount "x". The opening 160 may be formed as part of a primary molding process in which the drip chamber 120 is formed, or as a secondary process wherein the opening 160 is punched-out or otherwise removed from the side wall 158. As explained more fully below, the opening 60 is dimensioned to accommodate a sealing off by of a vent plug 162 to provide a self-priming function to the drip chamber 120.

The term "vent plug" as used herein means an obstruction for sealing off the opening 160. This can be accomplished, by way of non-limiting example, by a member dimensioned for seating within the opening 160 or by a cover or shield, such as a band of material. The vent plug may include various other types of plugs, including mechanically or chemically actuated plugs. The plug may be a bimetallic strip which is water activated. The vent plug may be activated by temperature, pressure, or chemical action. The vent plug may also be mechanically triggered.

The fluid drops 134 form a reservoir 164 at the bottom of the drip chamber 120. The liquid is then provided to the patient conduit 122 for conveying the liquid to the termination end 124, at which an end cap 170 that may be detachably or permanently connected, allows coupling of the patient line to an IV needle (not shown). The end cap 170 includes a side wall 171, a front wall 173 in which a vent 172 is formed, and a termination end vent plug 174. Also disposed on the patient conduit 122 is the roller clamp 150 having an adjustable control such as a knurled wheel 176 for regulating the flow of liquid in the patient conduit 122.

As fully discussed above, a problem with existing IV systems having drip chambers lies in the setup and "priming" of the drip chamber to establish a desired or prescribed medicament flow rate at which the medicament will enter the patient. As explained above, this typically requires a heath care professional, such as a nurse, to allow the medicament in the drip chamber to reach a certain level, typically ⅓ of the drip chamber volume. In order to accomplish this, the patient conduit 122 needs to be obstructed or otherwise partially closed off so that the liquid will fill the drip chamber 120 at a faster rate than the liquid enters the patient conduit 122 to form the reservoir 164. Thus, the health care professional will be required to tighten the roller clamp 150 for this purpose. Moreover, to set the reservoir level at approximately ⅓ of the drip chamber volume, an equal volume of air in the drip chamber must be removed. In pre-existing IV systems, this was accomplished by squeezing the flexible drip chamber side wall 158. In the event the squeezing of the drip chamber side wall 158 caused an excessive amount of air to be removed, this resulted in an excessive amount of liquid collected in the reservoir 164 which then needed to be removed in a tedious manner as explained above. Also, if the liquid entered the reservoir and/or patient line too rapidly, air bubbles will be formed on the inner surface of the patient conduit and then have to be removed, typically by tapping the chamber 120 and/or patient conduit 122.

In accordance with the present invention, the manual priming activity previously performed by health care professionals can be eliminated by the IV system 100. When the spike assembly 116 is first connected to a liquid container 112, liquid will begin to flow through the liquid conduit 142 into the funnel region 128, whereupon the drip orifice 132 will cause liquid drops 134 to be formed and fall, under the force of gravity, into the drip chamber 120. To facilitate formation of the reservoir 164 and, specifically, to prevent the liquid from draining into the patient conduit 122 before the reservoir 164 can be formed to a desired depth relative to the drip chamber bottom 154, liquid flow through the patient conduit 122 must be obstructed so that the medicament level will rise in the drip chamber at a rate which exceeds the flow of the medicament into the patient line. This can be accomplished by adjustment of the roller clamp 150, such as by manipulating adjustment wheel 176 or, as is contemplated by the preferred embodiment, through the vent 172 formed in the front wall 173 of the end cap 170. Thus, if the roller clamp 150 is in its fully opened state, the narrow opening of the vent 172 will restrict liquid flow in the patient conduit 122 to a rate which is slower than the rate that the fluid enters the drip chamber 120 so that the reservoir 164 can form in the drip chamber and so that fluid will enter the patient line at a slow rate to prevent the formation of air bubbles therein.

With flow in the patient conduit 122 restricted by the roller clamp 150 and/or by the end cap 170, liquid drops 134 continue to enter the drip chamber 120 so that the reservoir 164 will rise to a height of "x". This height corresponds to the opening 160 at which the vent plug 162 is disposed. In one embodiment, the vent plug 162 is comprised of an absorptive material which allows displaced air from the drip chamber 120—which is displaced by the increased level of the reservoir 164—to pass from the drip chamber to the surrounding atmosphere but which, upon contacting liquid, expands or swells to seal off the opening 160. When this occurs, liquid in the reservoir 164 is prevented from escaping through the vent plug 162 and air from the surrounding atmosphere is prevented from reentering the drip chamber 120 through the vent plug 162.

In this manner, the IV system 100 functions as a self-priming device which automatically allows the reservoir to fill to a desired level (e.g., ⅓ of the drip chamber volume) once the spike assembly 116 is attached to the liquid container 114 so that a health care professional no longer needs to compress the drip chamber side wall 158 to cause liquid to flow therein. Because the drip chamber no longer needs to be compressed for priming, the problem of over-filling the drip chamber is avoided. Consequently, the material used to form the drip chamber 120 is no longer limited to a flexible material but can now include rigid materials.

Suitable absorptive materials for the vent plug 162 include, by way of non-limiting example, porous PE, PP, or PTFE, embedded, doped or coated with carboxymethylcellulose (CMC), polyacrylate, or other known or hereafter discovered super-absorbent polymers.

To allow air present in the patient conduit 122 to escape through the termination end 124 so that, upon connection of the termination end 124 to a patient, such air will not enter the patient, the termination end vent plug 174 is provided. The termination end vent plug 174 is comprised of porous PE, PP, or PTFE, embedded, doped or coated with a super-absorbent polymer and creates a barrier when liquid impinges upon it. Alternatively, the termination end vent plug 174 can be formed of a hydrophobic material. Once the patient conduit 122 is completely filled with liquid, all air is removed therefrom and the termination end vent plug 174 forms a barrier to prevent spillage of the liquid through the vent 172. In this state, the IV system 100 is ready for attachment to a patient IV connection. This can be accomplished by detaching the end cap from the patient line and then coupling the line to a patient. The termination end vent plug 174 allows air from the patient conduit 122 to pass from the patient line to the surrounding atmosphere through vent 172 in the end cap 170. However, once the termination end vent plug becomes wet through contact with the liquid in the patient conduit 126, air is prohibited from reentering the patient line through the vent 172.

When connecting the already-primed IV system 100 to a subsequent medicament container, the health care professional simply closes the patient conduit 122 via the roller clamp 150, disconnects the spike 118 from the empty container, and attaches it to a full container. Any amount of liquid that may exist in the spike 118 during disconnection and reconnection to a medicament container is de minimis and will have little effect on the level of the reservoir 64. Once connected and the patient line reopened by opening the roller clamp, air in region 144 will be removed through membrane 146 and liquid will begin to flow into the drip chamber and into the patient conduit 122.

Another benefit of the inventive self-priming IV system 100 is that the occurrence of a high liquid flow rate into the drip chamber is reduced or altogether avoided because the primary cause of such a condition—the manual compressing of the drip chamber side wall 158—is no longer performed. Nevertheless, to prevent the vent plug 162 from prematurely contacting the liquid, such as when the drops 134 enter the drip chamber 120 and cause a splatter or splashing effect against the surface of the reservoir, a splash guard 178 formed of, for example, a liquid impervious plastic shield, can be readily affixed about the vent plug 162 to the internal surface of the side wall 158 of the drip chamber. As shown, the splash guard 176 is connected to the drip chamber side wall 158 by, for example, adhesive at a location above the vent plug 162, and extends to a point below the vent plug 162 and offset from the side wall 158 so that an opening 177 is formed to allow the rising reservoir 164 to contact the vent plug 162 in an intended manner.

It should be appreciated that the inventive drip chamber 120 and the vented end cap 170 can be used together in an IV system, or can be used separately, with the benefits attributed to each such feature being realized by that feature's use. For example, the drip chamber 16 can be used in conjunction with the roller clamp 150 by using the roller clamp to partially close off and restrict liquid flow in the patient conduit 126. This allows the reservoir 164 to fill to a desired level to moisten the vent plug 162 and also allows a slow rate of liquid to fill the patient conduit 126 and expel air therefrom through the termination end 124 without causing air bubbles to form on the inner surface of patient conduit 122. Such a system, however, still requires caregiver attention because the roller clamp 150 will need to be manipulated to adjust a desired flow rate for priming the drip chamber 120. Likewise, end cap 170 can be used at the termination end of a patient conduit 122 attached to any known IV delivery system, such as a system containing a drip chamber 120 or a system containing an infusion pump (not shown). The end cap 170, as explained above, will reduce the rate of liquid flow in the patient conduit 122 so that air bubbles will not be formed on the inner surface of the fluid conduit. Moreover, termination end vent plug 174 will prevent seepage of the liquid from the termination end 124 once the patient line becomes filled in the intended manner. If the end cap 170 is of a removable configuration, such as via a Luer-type connection as is known in the art, then once the patient conduit 122 is filled, roller clamp 150 will be closed and end cap 170 can then be removed without causing seepage of the liquid contained in the patient conduit 122, whereupon the conduit can then be attached to the intravenous needle connected to a patient. Thereafter, roller clamp 150 can be re-opened to allow intended operation of the IV system.

An additional feature illustrated in FIG. 3 is an extension conduit 180 is disposed between the spike assembly and drip chamber to transport the liquid from the spike assembly 116, and in particular, from the outlet 130 of the funnel portion 128, to the drip chamber 120. The extension conduit is comprised of a flexible tube material such as plastic, having a length "L", and which is preferably transparent or translucent. The extension conduit 180 has an inlet end 182 connected to the spike assembly outlet, and an outlet end 184 connected to, or otherwise disposed in, the drip chamber top wall 150. In this embodiment the drip orifice 132 may be formed in the outlet end 184 of the conduit or, may be formed in the drip chamber top wall 150. The length "L" of the conduit is sufficient to separate the relative distance between the spike assembly 116 and the drip chamber 120 so that the drip chamber is disposed at a height which is more readily viewable by the health care professional. This feature is desirable because the liquid bag or bottle may be positioned higher than the eye level of the health care professional making observation of the drip chamber and the counting of drops for flow rate adjustments will be difficult. The extension conduit 180 can be used in connection with any known IV system for separating a drip chamber from a spike assembly.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A self priming intravenous delivery system, comprising:
a coupling assembly for attaching the delivery system to a source of liquid and including a coupling membrane for controlling the flow of liquid and air through the coupling assembly;
a drip chamber having an inlet for receiving liquid through the coupling assembly, the drip chamber having a membrane for preventing air from leaving the drip chamber;
a self leveling port disposed within a wall of the drip chamber, the port being permeable to air, but impermeable to liquid, and becomes impermeable to air upon contact with liquid;
a patient conduit in fluid communication with a drip chamber outlet; and
a flow control plug disposed at the distal end of the patient conduit, wherein the flow control plug includes a housing that houses a single flow control material, wherein the flow control material is permeable to air but impermeable to liquid and controls fluid flow in the patient conduit during priming to reduce air bubble formation.

2. The self priming intravenous delivery system of claim 1 wherein the coupling further comprises an air evacuation filter.

3. The self priming intravenous delivery system of claim 1 further comprising a zero deadspace port on the patient conduit.

4. The self priming intravenous delivery system of claim 1 wherein the coupling assembly is vented.

5. The self priming intravenous delivery system of claim 1 wherein the coupling membrane is hydrophilic and stops fluid flow in the system when the fluid source is empty.

6. The self priming intravenous delivery system of claim 1 wherein the flow control plug is permeable to air until contacted by liquid, and wherein the flow control plug is further impermeable to liquid.

7. The self priming intravenous delivery system of claim 1 wherein the drip chamber membrane comprises a bubble trap.

8. The self priming intravenous delivery system of claim 1 further comprising an adjustable clamp on the patient conduit.

9. The self priming intravenous delivery system of claim 1 wherein the flow control material restricts the flow of liquid moving through the patient conduit such that the flow is generally laminar.

10. A method for priming a patient intravenous line comprising the steps of:

providing a self priming intravenous delivery system, comprising a coupling assembly for attaching the delivery system to a source of liquid and including a coupling membrane for controlling the flow of liquid and air through the coupling assembly; a drip chamber for receiving liquid through the coupling, the drip chamber having an inlet and an outlet, and having a membrane disposed therein for preventing air from leaving the drip chamber; a self leveling port disposed within a wall of the drip chamber being permeable to air, but impermeable to liquid; a patient conduit in fluid communication with the drip chamber; a flow control plug disposed at the distal end of the conduit, wherein the flow control plug includes a housing that houses a single flow control material, wherein the flow control material is permeable to air but impermeable to liquid; and attaching a source of fluid to the coupling assembly such that fluid flows into and through the delivery system without user intervention but such that the patient conduit is bubble free during system priming.

11. The method of claim 10 wherein the system further comprises an adjustable clamp on the patient conduit and further comprising the step of closing the clamp.

12. The method of claim 10 wherein the coupling further comprises an air evacuation filter.

13. The method of claim 10 further comprising the steps of attaching the patient conduit to a patient and initiating fluid flow to the patient where the patient conduit remains air bubble free during infusion and upon fluid source completion.

14. The method of claim 10 wherein in the system further comprises at least one zero deadspace port on the patient conduit.

15. The method of claim 10 wherein the coupling assembly is vented.

16. The method of claim 10 wherein the coupling membrane is hydrophilic.

17. The method of claim 10 wherein the flow control plug is hydrophobic.

18. The method of claim 10 wherein the drip chamber membrane comprises a bubble trap.

19. A self priming intravenous delivery system, comprising:

a coupling assembly for attaching the delivery system to a source of liquid and including a coupling membrane for controlling the flow of liquid and air through the coupling assembly;

a drip chamber having an inlet for receiving liquid through the coupling assembly, the drip chamber having a membrane for preventing air from leaving the drip chamber;

a self leveling port disposed within a wall of the drip chamber, the port comprising a filter which is permeable to air but impermeable to liquid, and which becomes impermeable to air upon contact with liquid;

a patient conduit in fluid communication with a drip chamber outlet; and a flow control plug disposed at the distal end of the patient conduit, wherein the flow control plug includes a housing that houses a single flow control material, wherein the flow control plug is permeable to air but impermeable to liquid and controls fluid flow in the patient conduit during priming to reduce air bubble formation, wherein the flow control plug is constructed such that it restricts the venting of air from the conduit as liquid flows through the conduit so that the volume of fluid flowing through the drip chamber inlet is greater than or about equal to the liquid flow through the chamber outlet until the self leveling port is closed.

20. The self priming intravenous delivery system of claim 19 wherein the self leveling port further comprises a valve which can be selectively opened and closed.

21. The self priming intravenous delivery system of claim 19 wherein the flow control material restricts the flow of liquid moving through the patient conduit such that the flow is generally laminar.

* * * * *